(12) United States Patent
Spratt

(10) Patent No.: US 8,226,238 B2
(45) Date of Patent: Jul. 24, 2012

(54) METHOD AND APPARATUS FOR SUBJECTIVE REFRACTION

(75) Inventor: Ray Steven Spratt, Petaluma, CA (US)

(73) Assignee: Carl Zeiss Vision Inc., Peteluma, CA (US)

( * ) Notice: Subject to any disclaimer, the term of this patent is extended or adjusted under 35 U.S.C. 154(b) by 0 days.

(21) Appl. No.: 12/703,501

(22) Filed: Feb. 10, 2010

(65) Prior Publication Data

US 2011/0194074 A1 Aug. 11, 2011

(51) Int. Cl.
*A61B 3/02* (2006.01)
(52) U.S. Cl. ........ 351/223; 351/176; 351/233; 351/246; 356/127
(58) Field of Classification Search .................. 351/222, 351/223, 234, 235, 239, 241, 242, 159, 160 R, 351/168–170, 175, 176; 356/124, 125, 127
See application file for complete search history.

(56) References Cited

U.S. PATENT DOCUMENTS

| 2,878,721 | A |   | 3/1959  | Kanolt |
|-----------|---|---|---------|--------|
| 3,751,138 | A |   | 8/1973  | Humphrey |
| 3,841,760 | A | * | 10/1974 | Guyton ......................... 356/124 |
| 3,880,502 | A | * | 4/1975  | Humphrey .................... 351/246 |
| 6,074,062 | A |   | 6/2000  | Morris et al. |

FOREIGN PATENT DOCUMENTS

GB 605 266 7/1948

OTHER PUBLICATIONS

European Search Report for corresponding EP Appl No. 11000675.6, dated Apr. 5, 2011.
European Search Report for corresponding EP Appl No. 11 000 675.6, dated Feb. 8, 2012.
http://en.wikipeda.org/wiki/Phoropter, this page was last modified on Jan. 17, 2012; bearing the date Feb. 22, 2012.

* cited by examiner

*Primary Examiner* — Huy K Mai
(74) *Attorney, Agent, or Firm* — Fish & Richardson P.C.

(57) ABSTRACT

An article for performing a subjective refraction includes a lens having a mean power that varies across the lens in a first direction and a cylindrical power that varies across the lens in a second direction, orthogonal to the first direction, wherein the mean power varies by four diopters or more and the cylindrical power varies by four diopters or more.

21 Claims, 7 Drawing Sheets

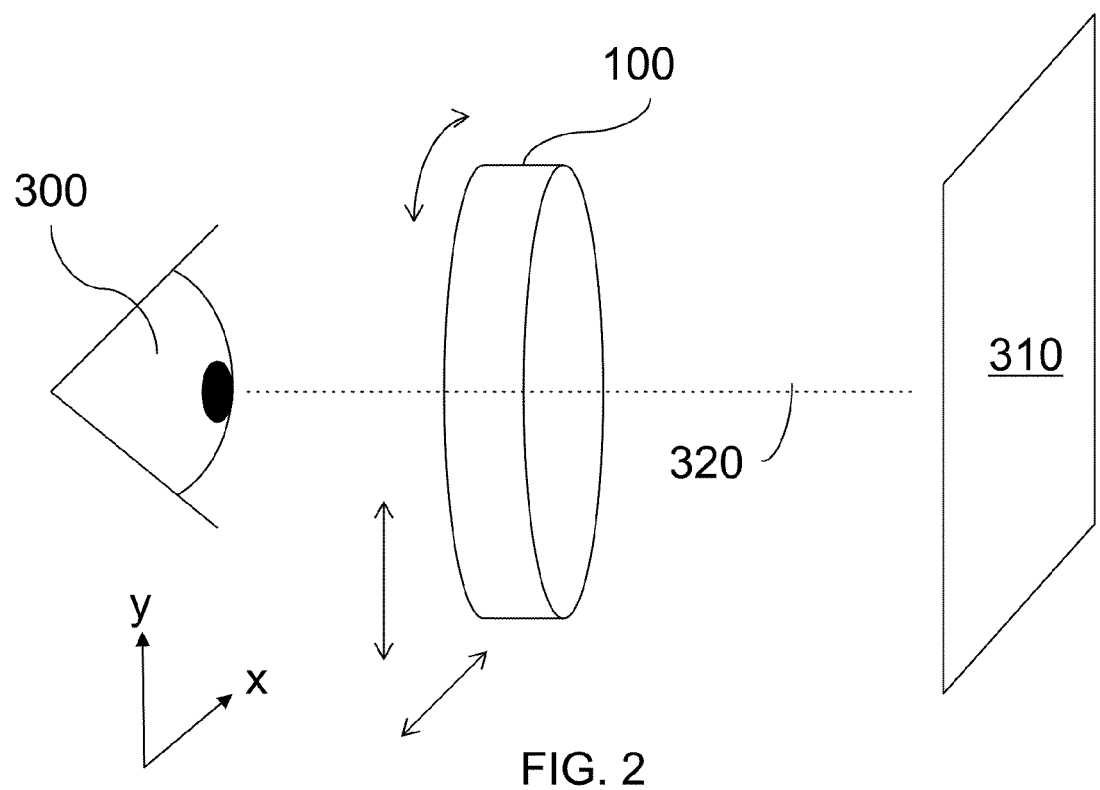
FIG. 2
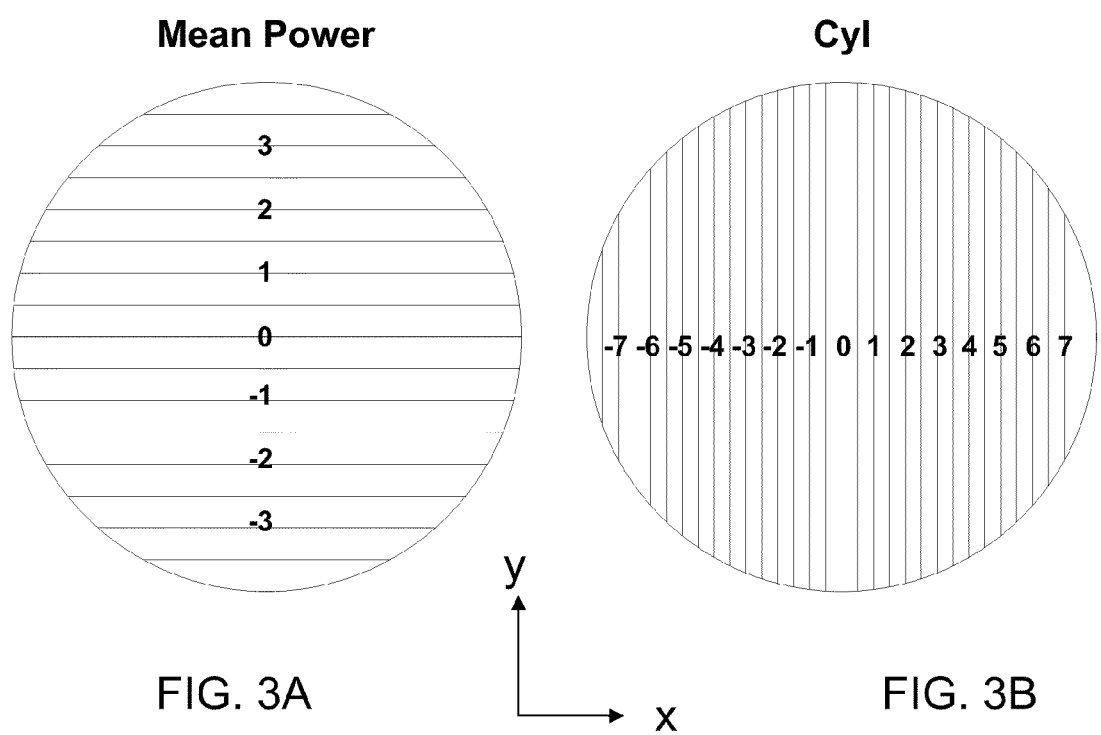
FIG. 3A
FIG. 3B

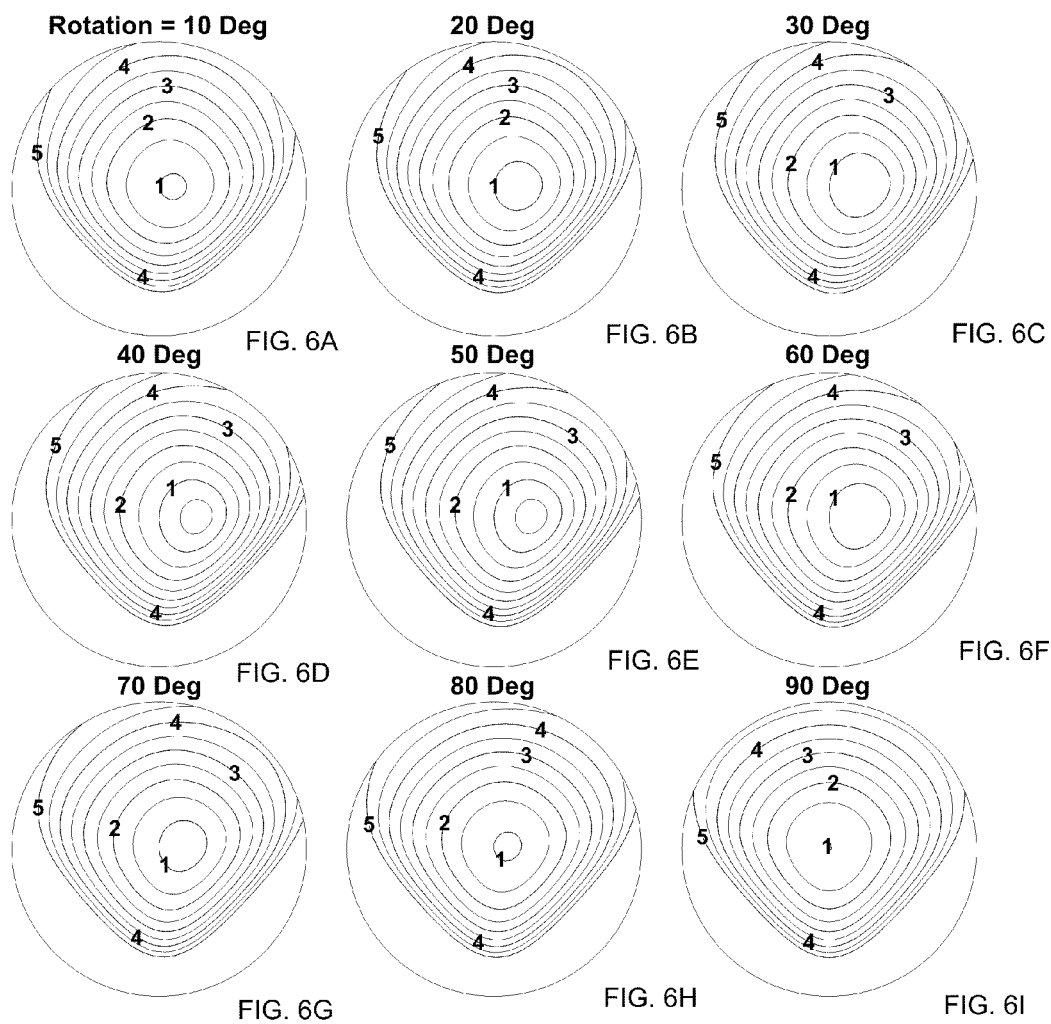

METHOD AND APPARATUS FOR SUBJECTIVE REFRACTION

TECHNICAL FIELD

This invention relates to methods and apparatus for performing a subjective refraction.

BACKGROUND

The vision-impaired human eye has refractive errors, which in first approximation can be described in terms of a spherical correction, a cylindrical power and an axis orientation. A spherical correction (referred to also simply as "sphere") corrects refractive error of the eye with a single convergent or divergent refractive power in all meridians. A cylindrical power ("cyl") corrects astigmatic refractive error of the eye by adding or subtracting power cylindrically in a meridian specified by the prescribed axis. The axis indicates the angle in degrees of one of two major meridians the prescribed cylindrical power is in. Which major meridian is referenced is indicated by the cyl being in plus or minus notation. The axis is measured on an imaginary semicircle with a horizontal baseline that starts with zero degrees in the 3 o'clock (or east) direction, and increases to 180 degrees in a counter-clockwise direction.

An eyeglass prescription ("Rx") specified by sphere, cyl, and axis is based on the assumption that the eyesight defect can be approximately corrected through a lens with a toroidal surface. An Rx can also be characterized by a "mean power" rather than sphere, where mean power refers to the average of the highest power along any meridian and the lowest power along any meridian of a toroidal lens. Note, further, that power refers to the back vertex power of a lens. An Rx is commonly determined using a subjective refraction. Subjective refractions are typically performed using a phoropter. These devices can be bulky and generally need to be run by trained experts.

SUMMARY

The inventor has recognized that the bulk of the complex array of lenses in a phoropter can be replaced by a few lenses (e.g., a single lens). For example, a single lens having a range of mean power in one direction and a range of cyl in the orthogonal direction can be used to perform a subjective refraction.

In general, in a first aspect, the invention features an article including a lens having a mean power that varies across the lens in a first direction and a cylindrical power that varies across the lens in a second direction, orthogonal to the first direction, wherein the mean power varies by four diopters or more and the cylindrical power varies by four diopters or more.

Embodiments of the article can include one or more of the following features. For example, the lens can include a first portion having a first axis orientation and a second portion having a second axis orientation, different from the first axis orientation. The first axis orientation can be at 45° with respect to the first direction. The second axis orientation can be orthogonal to the first axis orientation. Embodiments can include one or more additional portions having axes orientations different from the first and second portions. The cylindrical power can vary monotonically in the second direction in the first portion and varies monotonically (e.g., linearly) in the second direction in the second portion. In some embodiments, the cylindrical power varies by four diopters or more (e.g., five diopters or more, six diopters or more, seven diopters or more, eight diopters or more) in the first portion and by four diopters or more (e.g., five diopters or more, six diopters or more, seven diopters or more, eight diopters or more) in the second portion. The cylindrical power can vary from 0 to 7.5 diopters or more in the first portion. Additionally, the cylindrical power can vary from 0 to 7.5 diopters or more in the second portion. The cylindrical power can vary linearly in the second direction in the first and second portions.

In some embodiments, the mean power varies from −4 diopters or less (e.g., −5 diopters or less, −6 diopters or less, −7 diopters or less, −8 diopters or less) to +4 diopters or more (e.g., +5 diopters or more, +6 diopters or more, +7 diopters or more, +8 diopters or more) in the first direction. The mean power can vary monotonically in the first direction. For example, the mean power can vary linearly in the first direction.

In some embodiments, the lens includes a plurality of zones extending along the second direction, each zone having a different mean power. The mean power of adjacent zones can vary by 0.25 diopters or more (e.g., 0.3 diopters or more, 0.4 diopters or more, 0.5 diopters or more, 0.75 diopters or more, 1 diopter or more).

The lens can include one or more scales identifying regions of different mean power or regions of different cylindrical power. In some embodiments, the lens includes a scale circumferentially disposed around the lens identifying different azimuths with respect to a lens axis.

In a further aspect, the invention features an apparatus that includes the article of the first aspect and a second lens having a constant mean power disposed relative to the article so that a viewer can observer a target through the second lens and the lens having the varying spherical and cylindrical powers.

In another aspect, the invention features a system that includes an optical arrangement including the article of the first aspect and a target, a user interface coupled to the optical arrangement and configured to allow a user to vary a position of the article with respect to the target, and an electronic controller in communication with the optical arrangement, wherein during operation a user positions the article relative to the target to determine a position of best vision for the user and the electronic controller determines an Rx for the user based on the position of best vision. The system can include a dispensing station in communication with the electronic controller, wherein during operation the dispensing station delivers eyeglasses or contact lenses to the user based on the Rx.

In general, in a further aspect, the invention features an article that includes a lens having a mean power that varies monotonically across the lens in a first direction and a cylindrical power that varies across the lens in a second direction, orthogonal to the first direction, the lens including a first portion having a first axis orientation and a second portion having a second axis orientation, different from the first axis orientation. Embodiments of the article can include one or more of the features described above with respect to the foregoing aspects.

In general, in a further aspect, the invention features a method that includes moving a lens relative to a patient, the lens having a mean power that varies across the lens in a first direction and a cylindrical power that varies across the lens in a second direction, orthogonal to the first direction; identifying a position on the lens through which the patient most clearly sees a target; and determining an Rx for the patient based on the identified position. The method can be implemented using the articles and systems described above in connection with the foregoing aspects.

Among other advantages, embodiments can include devices for performing a subjective refraction that are light, inexpensive, portable and/or easy enough to use that refractions by semi-skilled individuals or even self refraction may be possible. For example, a single, hand-held optical element can be used to perform a subjective refraction, allowing subjective refractions to be performed in areas where the population does not have ready access to phoropters (e.g., rural areas in, for example, developing countries).

The details of one or more embodiments are set forth in the accompanying drawings and the description below. Other features and advantages will be apparent from the description and drawings, and from the claims.

DESCRIPTION OF DRAWINGS

FIG. 2 is a schematic diagram showing a method for using the lens shown in FIGS. 1A and 1B to perform a subjective refraction.

FIGS. 3A and 3B show plots of mean power and cyl values, respectively, on an embodiment of a lens.

FIGS. 6A-6I are blur plots for different rotations of a lens (in 10° increments) for the Rx corresponding to the blur plots in FIGS. 5A and 5B.

Like reference symbols in the various drawings indicate like elements.

DETAILED DESCRIPTION

Figure 1A:
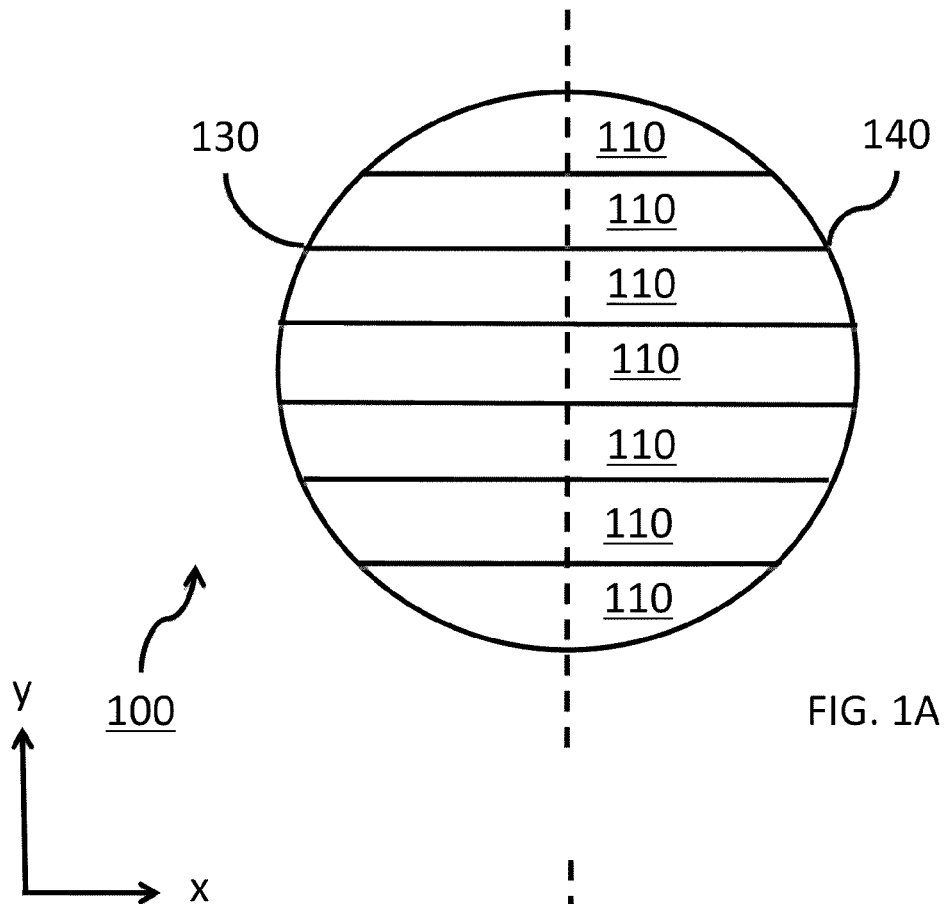
FIGS. 1A and 1B are schematic diagrams showing a lens having zones in orthogonal directions.
Figure 1B:
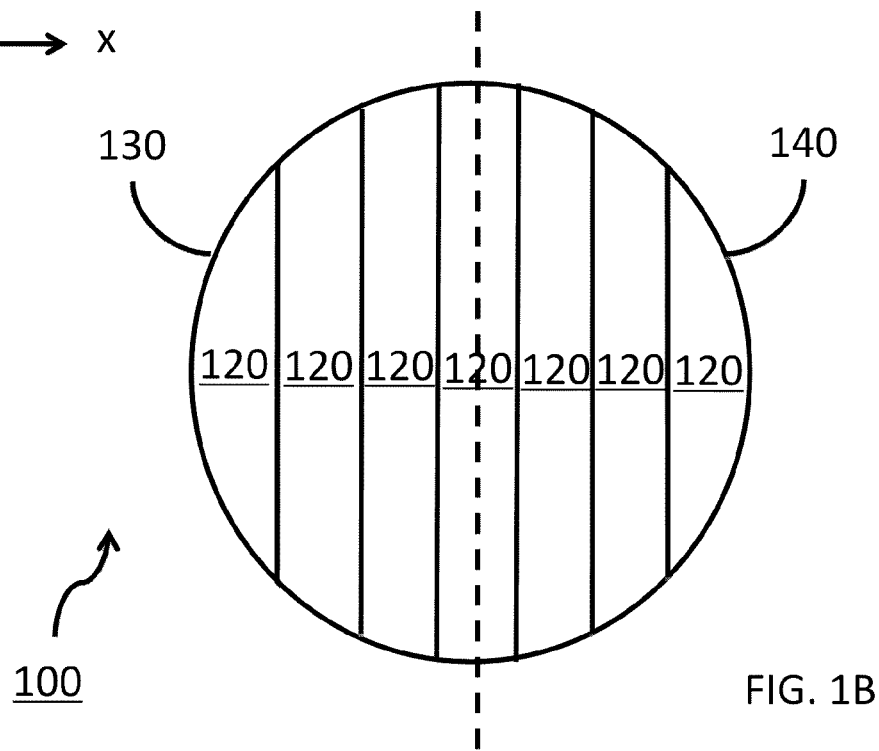

Referring to FIGS. 1A and 1B, a lens 100 has regions of differing refractive power that span a range of different mean powers and a range of cyl values. In addition, lens 100 has two portions with differing axis orientations. Specifically, referring to the Cartesian co-ordinate system shown, the mean power of lens 100 varies along the y-direction while cyl varies along the x-direction. Accordingly, lens 100 can be considered to include a number of zones 110 in the y-direction, each having a different mean power, and can be considered to have a number of zones 120 in the x-direction, each having a different cyl. Along the x-direction, lens 100 also has two portions 130 and 140 that have differing axis orientations. For example, portion 130 can have an axis orientation of 45° (measured counter-clockwise from the x-axis), while portion 140 has an axis orientation of 135°. Each portion 130 and 140 includes zones 120 that have different values for cyl. Typically, mean power and cyl vary smoothly across lens 100, in which case the boundaries between zones 110 simply represent mean power contours and the boundaries between zones 120 represent cyl contours. In some embodiments, lens 100 has discrete transitions from one zone to the next.

Zones 110 span a range of mean powers corresponding to mean powers typical of many Rx's. For example, zones 110 can span a range from −2 or less to +2 diopters or more (e.g., from −3 or less to +3 diopters or more, from −4 or less to +4 diopters or more, from −5 or less to +5 diopters or more, from −6 or less to +6 diopters or more). In some embodiments, zones 110 span a range of positive mean powers (e.g., from 0 to +5 diopters or more, from 0 to +6 diopters or more, from 0 to +7 diopters or more, from 0 to +8 diopters or more) or a range of negative mean powers (e.g., from −5 to 0 diopters, from −6 to 0 diopters, from −7 to 0 diopters, from −8 to 0 diopters, from −10 to 0 diopters, from −12 to 0 diopters).

Mean power can vary monotonically across lens 100 in the y-direction. In other words, mean power increases from the lowest mean power on one side of lens 100 to the highest mean power on the opposite side. In some embodiments, mean power varies linearly along the y-direction. In embodiments where zones 110 have a discrete transition in mean power from one to the next, the mean power of adjacent zones varies by a constant increment. For example, the average mean power of adjacent zones can vary in increments of 0.1 diopters or more (e.g., 0.25 diopters or more, 0.5 diopters or more).

In each portion 130 and 140, zones 120 span a range of values for cyl corresponding to values typical of many Rx's. For example, in portions 130 and/or 140, cyl can vary from 0 to 5 diopters or more (e.g., from 0 to 6 diopters or more, from 0 to 7 diopters or more, from 0 to 8 diopters or more). Cyl in each portion 130 and/or 140 can vary monotonically. In some embodiments, cyl in each portion 130 and 140 varies linearly. In embodiments where zones 120 have a discrete transition in cyl from one zone to the next, cyl of adjacent zones in each portion can vary by a constant increment. For example, average cyl of adjacent zones in each portion can vary in increments of 0.1 diopters or more (e.g., 0.25 diopters or more, 0.5 diopters or more).

While zones 110 are depicted as having the same width in the y-direction, in general, in embodiments where zones 110 represent discrete transitions in mean power, the width of each zone 110 in the y-direction can be the same or different as the other zones. Similarly, in such embodiments, the width of each zone 120 in the x-direction can be the same or different as other zones. In general, the width of zones 110 and 120 are sufficiently large to allow a patient to accurately identify which zones correspond to the best viewing position. In some embodiments, each zone has a width of 2 millimeters or more (e.g., 3 millimeters or more, 4 millimeters or more, 5 millimeters or more).

Furthermore, while lens 100 is depicted as having seven zones 110 and seven zones 120, in general, in embodiments where the zones represent discrete transitions in mean power and cyl, the number of zones in either direction can vary as desired. Generally, the number of zones in each direction is selected to so that lens 100 has sufficient range of mean powers and cyl to assess a wide range of prescriptions. However, the number of zones 110 and 120 are typically constrained by the lens size and need to make the zones sufficiently large so that a patient can accurately identify a which zones correspond to the position of best viewing. In some embodiments, lens 100 has 10 or more (e.g., 12 or more, 15 or more, 18 or more, 20 or more) zones 110 in the y-direction. In certain embodiments, lens 100 has 10 or more (e.g., 12 or more, 15 or more, 18 or more, 20 or more) zones 120 in the x-direction. In general, the number of zones 110 in the y-direction can be the same as or different from the number of zones 120 in the x-direction.

In general, the size and shape of lens 100 can vary as desired. As depicted in FIGS. 1A and 1B, in some embodiments, lens 100 is round. Other shapes are also possible. For example, oval and polygonal (e.g., square or rectangular) shaped lenses can be used. Typically, lens 100 is sufficiently large to accommodate a wide range of mean power and cyl in respective directions, without the gradient of change in mean power and/or cyl being so great so that a patient cannot readily accurately identify where on the lens corresponds to the position of best viewing. Lens 100 can have a maximum dimension in a range from about 50 mm to about 200 mm. In certain embodiments, lens 100 can be formed using conventional 80 mm blank.

Lens 100 can be formed from a variety of different materials. In general, the materials are substantially transparent in the visible portion of the electromagnetic spectrum (e.g., wavelengths from about 400 nm to about 700 nm). Exemplary materials include both inorganic materials and organic materials. Inorganic materials that can be used include glasses such as BK7 and crystalline materials such as quartz. Inorganic materials that can be used include polymers such as polycarbonate.

In general, lens 100 can be constructed so that only one surface of the lens includes the curvature that provides the varying mean power and cyl, while the opposite surface is flat or spherical, for example. In certain embodiments, lens 100 can be constructed so that the two opposite surfaces are shaped to provide the varying mean power and cyl. For example, one surface can be formed to provide the varying mean power in one direction, while the opposite surface is formed to provide varying cyl in the orthogonal direction.

Moreover, in general, lens 100 can be formed from a single piece of material, or from two or more pieces of material. For example, in some embodiments, lens 100 can be formed by optically coupling a first piece of material having a surface formed to provide varying mean power in one direction with a second piece of material having a surface formed to provide vary cyl in the orthogonal direction.

Referring to FIG. 2, lens 100 can be used for subjective refraction as follows. A patient 300 holds the lens in front of one eye and looks at a large distant uniform target 310, such as a rectangular grid of small spots, for example, along an axis 320. The patient translates lens 100 in the x- and y-directions and rotates lens 100 about axis 320 until the patient identifies the location and angular orientation of lens 100 that provides the least blurred view of target 310. The patient's Rx can then be identified simply from this location and angular orientation.

FIGS. 3A and 3B show plots of the mean power and cyl for an example of such a lens, contoured in 0.50 diopter steps. This example covers a range of +4 to −4 diopters in mean power over a lens having a diameter of 80 mm. This lens covers a full 0 to 4 diopters of cyl for mean powers ranging from a +/−3 diopters. The cyl axis on the right hand side of the lens is 135°, while on the left hand side is 45° degrees.

Figure 4A:
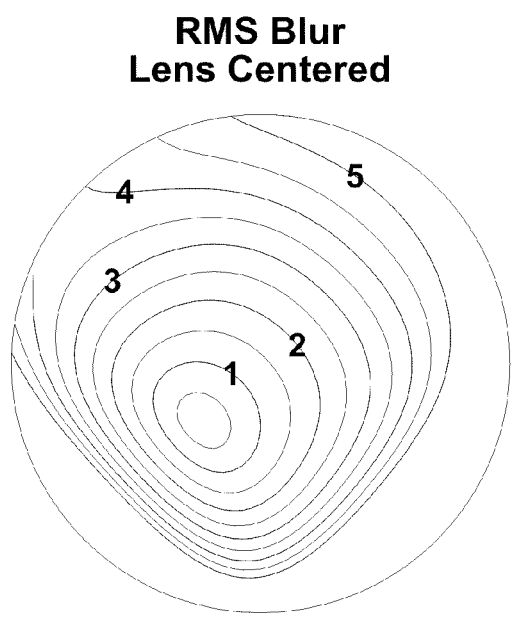
FIGS. 4A and 4B are exemplary blur plots for a specific Rx with the lens centered and blur centered, respectively.
Figure 4B:
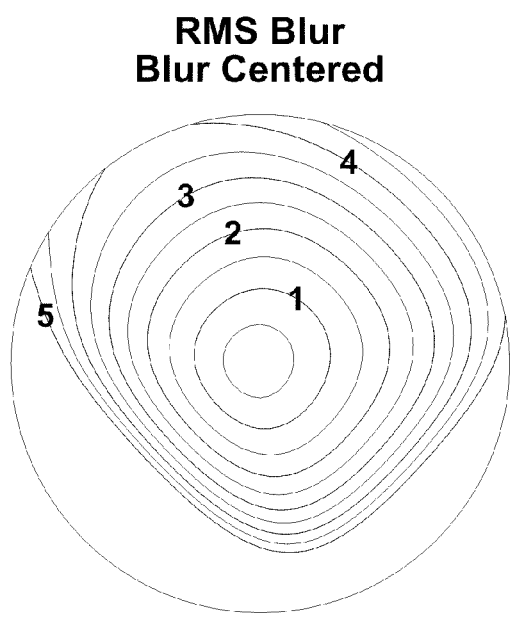

For this example, assume a patient's Rx is +2 diopters for mean power, −2 diopters cyl at 45°. FIG. 4A shows a ray-traced blur plot (RMS spot size) when the patient holds the lens centered in front of his eye. The blur plots are determined by ray-tracing an object through the lens-eye combination. The ray-trace is a numerical calculation done using mathematical models for the eye and the lens. Such ray tracing can be performed used commercially-available software, such as Zemax and Code V. As shown here, blur has the units of diopters so that 1 diopter of error in the prescription causes 1 diopter of blur. These blur plots show how much degradation of the image the wearer will perceive when looking through various parts of the lens. The region of clear vision, minimum blur, is well off the center of the lens. If the patient simply translates the lens, while keeping the back surface of the lens perpendicular to the line of sight, until the region of clear vision is in the center of his field of view, the patient's resulting view corresponds to the blur plot shown in FIG. 4B. To achieve this, the patient would have translated the lens 10 mm up and 10 mm to the right. The patient, or an observer, identifies that location of the lens, e.g., using a pen. The patient's Rx is then read directly off the point on the lens surface.

Figure 5A:
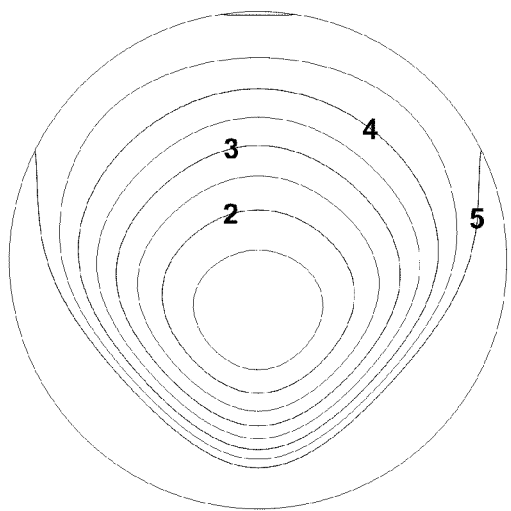
FIGS. 5A and 5B are exemplary blur plots for another specific Rx with the lens centered and blur centered, respectively.
Figure 5B:
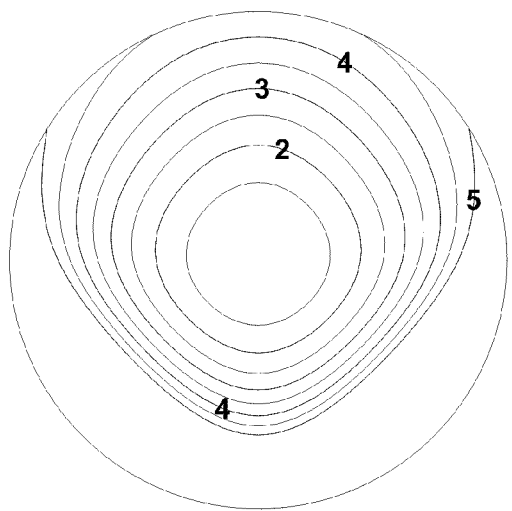

Of course, for the lens shown in FIGS. 3A and 3B and described above, only Rx's with cyl axis at 45° or 135° can be "resolved" with a pure translation. For other axis orientations, a rotation is necessary. For example, consider another patient whose Rx is +2 diopters for mean power, −2 diopters cyl at 180°. FIG. 5A shows a blur plot for this prescription with the lens centered. In this case, for translations of the lens only, the minimum blur is at +1.0 diopter for mean power and occurs along the y-axis. After the lens is translated to center the blur (FIG. 5B), the minimum blur is still at +1 diopter. Thus, if one were to read the Rx here they would get an erroneous reading of +1 spherical. This would actually correspond to the correct value for mean power, but would miss the cyl all together. To determine the cyl, and the cyl axis, the lens must be rotated.

FIGS. 6A-6I show blur plots for various rotation angles from 10° to 90°, keeping the same point of the lens in front of the patient's eye. As the lens is rotated through 90° the minimum blur smoothly changes, reaching a minimum around 45° degrees of rotation and also translates. The procedure is then to translate the lens in the x- and/or y-directions while maintaining its orientation until the minimum blur is at the center of the field of view. At this point the mean power and cyl can be read from the location in front of the eye, and the axis can be inferred from the rotation of the lens.

Notice that only 90° degrees of rotation is necessary to search the full 180° degrees of possible axis values. This is because the left side of the lens is has a cyl axis that is rotated 90° degrees relative to the left. So one side or the other of the test lens will show a minimum cyl for any Rx cyl with only a 90° search.

In general, one can read the Rx from the location and orientation of the lens in a variety of ways. For example, as mentioned previously, the point on the lens corresponding to minimum blur could be marked (e.g., using a pen) and the power could then be read using a lensmeter (e.g., a vertometer).

Figure 7:
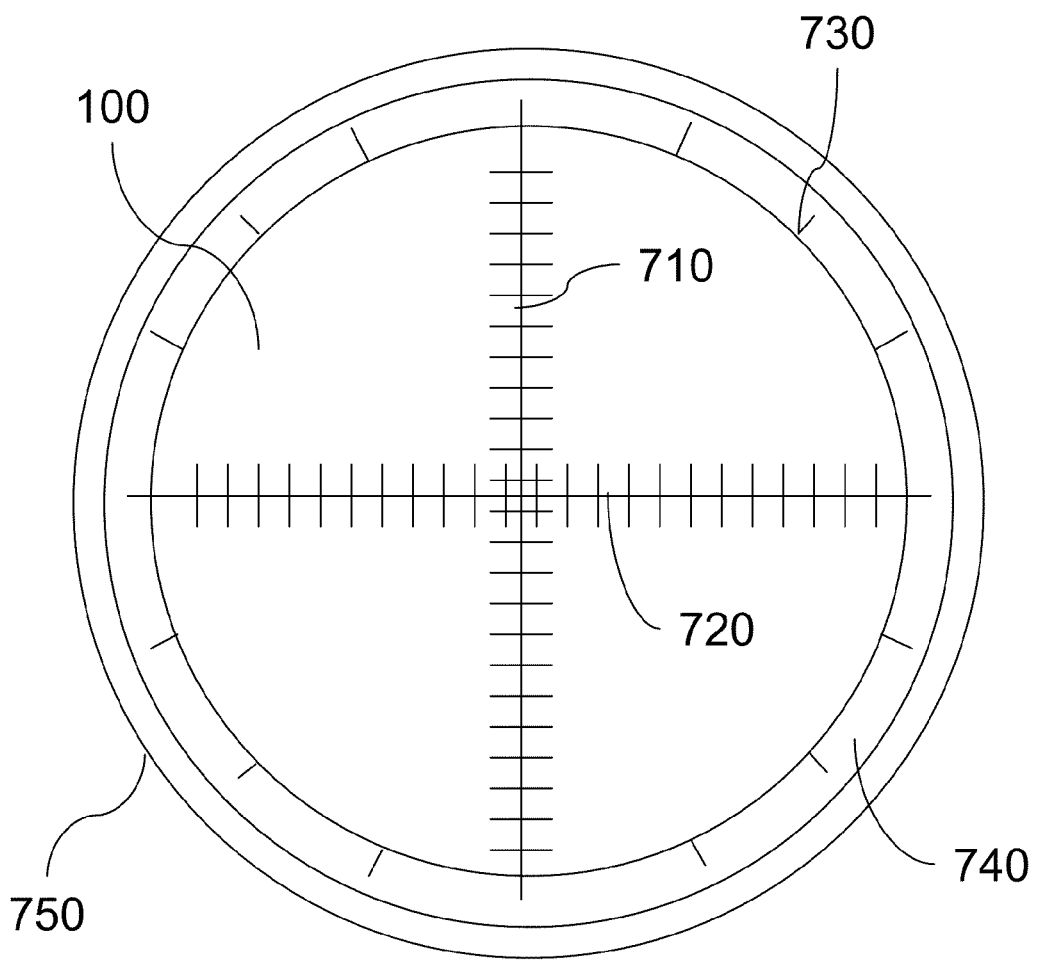
FIG. 7 is a schematic diagram of a lens having grid lines in rotating mount.

Referring to FIG. 7, in some embodiments, lens 100 is provided with grid lines 710 and 720 to allow one to read the Rx directly off the lens surface. Here, grid lines 710 extend in the y-direction and provide a scale for reading mean power, while grid lines 720 extend in the x-direction and provide a scale for reading cyl. The grid lines can be etched or printed onto the surface of lens 100, for example.

Alternatively, or additionally, grid lines 730 can be provided circumferentially around the end of lens 100, providing angular orientation values.

In certain embodiments, lens 100 is attached to a lens mount 740 that includes grid lines 730 for angular orientation. Lens mount 740 can include a rotating bezel 750, allowing for easy rotating of lens 100 within the mount.

Figure 8:
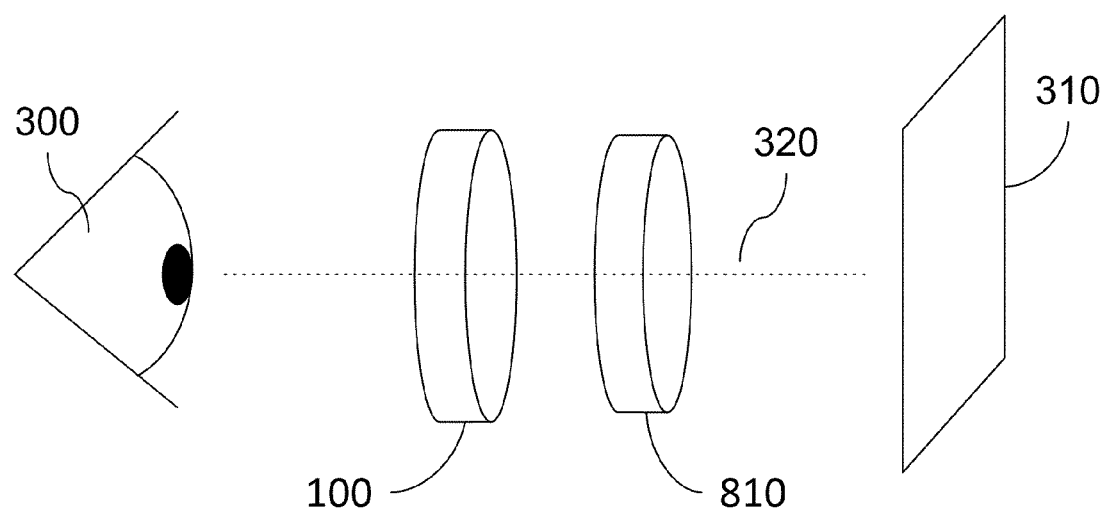
FIG. 8 is a diagram showing a system composed of two lenses.

While the foregoing discussion involves only a single lens for use in performing a subjective refraction, in general, more than one lens can be used. For example, a set of a few lenses could be used to cover the full Rx range of a typical lens product (e.g., from +8 to −12 diopters for mean power with up to 4 diopters of cyl). Referring to FIG. 8, in some embodiments, lens 100 is supplemented using a second lens 810, e.g., in the form of a small set of spherical eyeglasses. Using the exemplary lens described above in connection with FIGS. 3A and 3B, which covers 4 diopters of cyl for +/−3 diopters of mean power, one could supplement this lens with an additional lens providing a lens system that spans a greater range of mean powers than the exemplary lens alone. For example, the single +3 to −3 lens can be used along with spherical spectacles having powers of +5, −5 and −10 diopters to provide a system that has an Rx range capability from +8 to −13 diopters of mean power. Specifically, the spherical spectacles having +5 diopters and the lens provides a range of mean powers from +8 to +2 diopters, the −5 diopter spectacles provides a range from −2 to −8 diopters, and the −10 diopters spectacles provides a range from −7 to −13 diopters.

Figure 9:
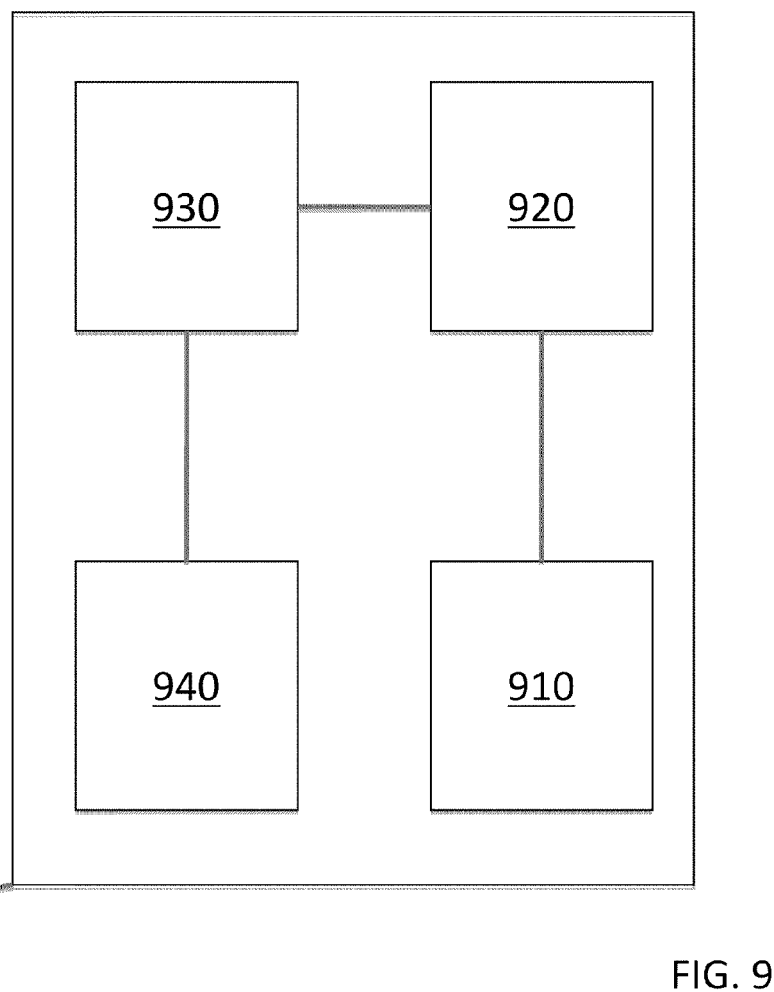
FIG. 9 is a schematic diagram of an embodiment of a kiosk.

While the foregoing embodiments feature relatively simple arrangements, more complex systems are also contemplated. For example, referring to FIG. 9, in some embodiments, one or more lenses can be used in a kiosk system 900 that can enable a patient to obtain an Rx and dispense either eyeglasses or contact lenses in accordance therewith, e.g., without assistance from an eyecare professional.

Kiosk 900 includes a user interface 910, an optical arrangement 920, an electronic controller 930 and a storage and dispensing station 940. Optical arrangement 920 includes a lens or system of lenses as described above, and a target. Optical arrangement also includes actuators, which are arranged to translate and rotate the lens(es) to allow a user to locate the position and orientation of best focus for the lens(es). User interface 910 includes, e.g., keyboard and/or joystick coupled to the actuators in optical arrangement 920. User interface 910 facilitates user interaction with the kiosk, allowing a user to enter information and manipulate the lens(es) to find the position of best vision for each eye. In some embodiments, optical arrangement includes optical elements for one eye, only, and the user sequentially locates the position of best vision for each eye individually. Alternatively, in certain embodiments, optical arrangement 920 can include optical elements that allow the user to find the position of best vision for both eyes together. For example, optical arrangement 920 can include two identical sets of lenses, each arranged to allow a patient to view a target through a corresponding set simultaneously.

Electronic controller (e.g., including a computer processor, memory, storage, and networking components) interfaces with user interface 910 and optical arrangement 920 to receive information about the position of best vision for each eye. Based on this information, electronic controller submits an Rx to storage and dispensing station 940, which retrieves and dispenses eyeglasses or contact lenses to the user.

Alternatively, or in addition to dispensing eyeglasses or contact lenses, system 900 can transmit the patients Rx to an optical laboratory or eyecare professional's office (e.g., using networking components) where corrective lenses can be made.

A number of embodiments of the invention have been described. Other embodiments are within the scope of the following claims.

What is claimed is:

1. An article, comprising:
    a single lens having a mean power that varies across the single lens in a first direction and a cylindrical power that varies across the single lens in a second direction, orthogonal to the first direction,
    wherein the mean power varies by four diopters or more and the cylindrical power varies by four diopters or more.

2. The article of claim 1, wherein the single lens comprises a first portion having a first axis orientation and a second portion having a second axis orientation, different from the first axis orientation.

3. The article of claim 2, wherein first axis orientation is at 45° with respect to the first direction.

4. The article of claim 3, wherein the second axis orientation is orthogonal to the first axis orientation.

5. The article of claim 2, wherein the cylindrical power varies monotonically in the second direction in the first portion and varies monotonically in the second direction in the second portion.

6. The article of claim 2, wherein the cylindrical power varies by four diopters or more in the first portion and by four diopters or more in the second portion.

7. The article of claim 2, wherein the cylindrical power varies from 0 to 7.5 diopters or more in the first portion.

8. The article of claim 7, wherein the cylindrical power varies from 0 to 7.5 diopters or more in the second portion.

9. The article of claim 2, wherein the cylindrical power varies linearly in the second direction in the first and second portions.

10. The article of claim 1, wherein the mean power varies from −4 diopters or less to +4 diopters or more in the first direction.

11. The article of claim 1, wherein the mean power varies monotonically in the first direction.

12. The article of claim 1, wherein the mean power varies linearly in the first direction.

13. The article of claim 12, wherein the single lens comprises a plurality of zones extending along the second direction, each zone having a different mean power.

14. The article of claim 13, wherein the mean power of adjacent zones vary by 0.25 diopters or more.

15. The article of claim 1, wherein the single lens comprises one or more scales identifying regions of different mean power or regions of different cylindrical power.

16. The article of claim 1, further comprising a scale circumferentially disposed around the single lens identifying different azimuths with respect to a lens axis.

17. An apparatus, comprising:
    the article of claim 1; and
    a second lens having a constant mean power disposed relative to the article so that a viewer can observer a target through the second lens and the single lens having the varying mean and cylindrical powers.

18. A system, comprising:
    an optical arrangement comprising an article and a target;
    the article comprising:
        a lens having a mean power that varies across the lens in a first direction and a cylindrical power that varies across the lens in a second direction, orthogonal to the first direction,
    a user interface coupled to the optical arrangement and configured to allow a user to vary a position of the article with respect to the target;
    an electronic controller in communication with the optical arrangement,
    wherein:
        the mean power varies by four diopters or more and the cylindrical power varies by four diopters or more and
        during operation a user positions the article relative to the target to determine a position of best vision for the user and the electronic controller determines an Rx for the user based on the position of best vision.

19. The system of claim 18, further comprising a dispensing station in communication with the electronic controller, wherein during operation the dispensing station delivers eyeglasses or contact lenses to the user based on the Rx.

20. An article, comprising:
    a single lens having a mean power that varies monotonically across the single lens in a first direction and a cylindrical power that varies across the single lens in a second direction, orthogonal to the first direction, the single lens comprising a first portion having a first axis orientation and a second portion having a second axis orientation, different from the first axis orientation.

21. A method, comprising:

moving a single lens relative to a patient while the patient observes a target through only the single lens, the single lens having a mean power that varies across the single lens in a first direction and a cylindrical power that varies across the single lens in a second direction, orthogonal to the first direction;

identifying a position on the single lens through which the patient most clearly sees the target; and determining an Rx for the patient based on the identified position.

* * * * *

UNITED STATES PATENT AND TRADEMARK OFFICE
CERTIFICATE OF CORRECTION

PATENT NO. : 8,226,238 B2
APPLICATION NO. : 12/703501
DATED : July 24, 2012
INVENTOR(S) : Ray Steven Spratt It is certified that error appears in the above-identified patent and that said Letters Patent is hereby corrected as shown below:

Title Page, Col. 1, Item (73) (Assignee),
Line 1, Delete "Peteluma," and insert --Petaluma,--

Title Page, Col. 2, Item (56) (Other Publications),
Line 5, Delete "wikipeda.org" and insert --wikipedia.org--

Column 8,
Line 55, Delete "more and" and insert --more; and--

Signed and Sealed this
Sixteenth Day of October, 2012

David J. Kappos
*Director of the United States Patent and Trademark Office*